United States Patent [19]

Camp

[11] Patent Number: 5,133,219

[45] Date of Patent: Jul. 28, 1992

[54] DYNAMICALLY BALANCED, DIFFERENTIAL GAS ADSORPTION APPARTAUS

[75] Inventor: Ronnie W. Camp, Duluth, Ga.

[73] Assignee: Micromeritics Instrument Corporation, Norcross, Ga.

[21] Appl. No.: 662,284

[22] Filed: Feb. 28, 1991

[51] Int. Cl.⁵ .............................................. G01N 15/08
[52] U.S. Cl. .................................................. 73/865.5
[58] Field of Search ................................ 73/865.5, 38

[56] References Cited

U.S. PATENT DOCUMENTS

| | | |
|---|---|---|
| 2,729,969 | 1/1956 | Innes . |
| 2,960,870 | 11/1959 | Nelson et al. . |
| 3,059,478 | 10/1962 | Coggeshall et al. . |
| 3,262,319 | 7/1966 | Orr, Jr. et al. . |
| 3,349,625 | 10/1967 | Benusa et al. . |
| 3,464,273 | 9/1969 | Hendrix et al. . |
| 3,555,912 | 1/1971 | Lowell . |
| 3,707,870 | 1/1973 | Herve et al. . |
| 3,850,040 | 11/1974 | Orr, Jr. et al. . |
| 4,083,228 | 4/1978 | Turner et al. . |
| 4,489,593 | 12/1984 | Pieters et al. . |
| 4,496,249 | 1/1985 | Lee et al. . |
| 4,566,326 | 1/1986 | Lowell . |
| 4,718,270 | 1/1988 | Storr . |
| 4,762,010 | 8/1988 | Borghard et al. . |
| 4,854,157 | 8/1989 | Wilson ................................. 73/38 |

FOREIGN PATENT DOCUMENTS 1057798 5/1959 Fed. Rep. of Germany .

OTHER PUBLICATIONS

"Particle Measurement" Brochure-Strohlein Laboratory and Measurement Technology.
"Strohlein AREA-Meter" brochure.
Bosch H. and Peppelenbos, A., "Automatic and Low Cost Determination of BET Surface Areas" J. of Physics E: Scientific Instruments 1977, pp. 605-608.

Primary Examiner—Robert Raevis
Attorney, Agent, or Firm—Jones, Askew & Lunsford

[57] ABSTRACT

An apparatus and method are disclosed for obtaining adsorption data to be used for surface area and pore volume analysis. The apparatus and method utilize the differential pressures between a pair of dosing systems to indicate the amount of gas adsorbed by a sample. The system doses a sample chamber and a null chamber from essentially equal volumes of gas, and causes the chambers to be dosed such that any pressure difference between them, caused by adsorption, is eliminated. The resulting differential pressure between the essentially equal volumes of gas then indicates the amount of gas adsorbed by the sample. The system may be operated to dose in equilibrated increments or in a scanning mode in which adsorbate gas is continuously leaked into the sample chamber. A feedback circuit then controls dosing into the null chamber to eliminate the pressure difference caused by adsorption onto the sample surface. A differential pressure transducer connecting the volumes from which the gas is released then indicates the amount of gas adsorbed.

28 Claims, 10 Drawing Sheets

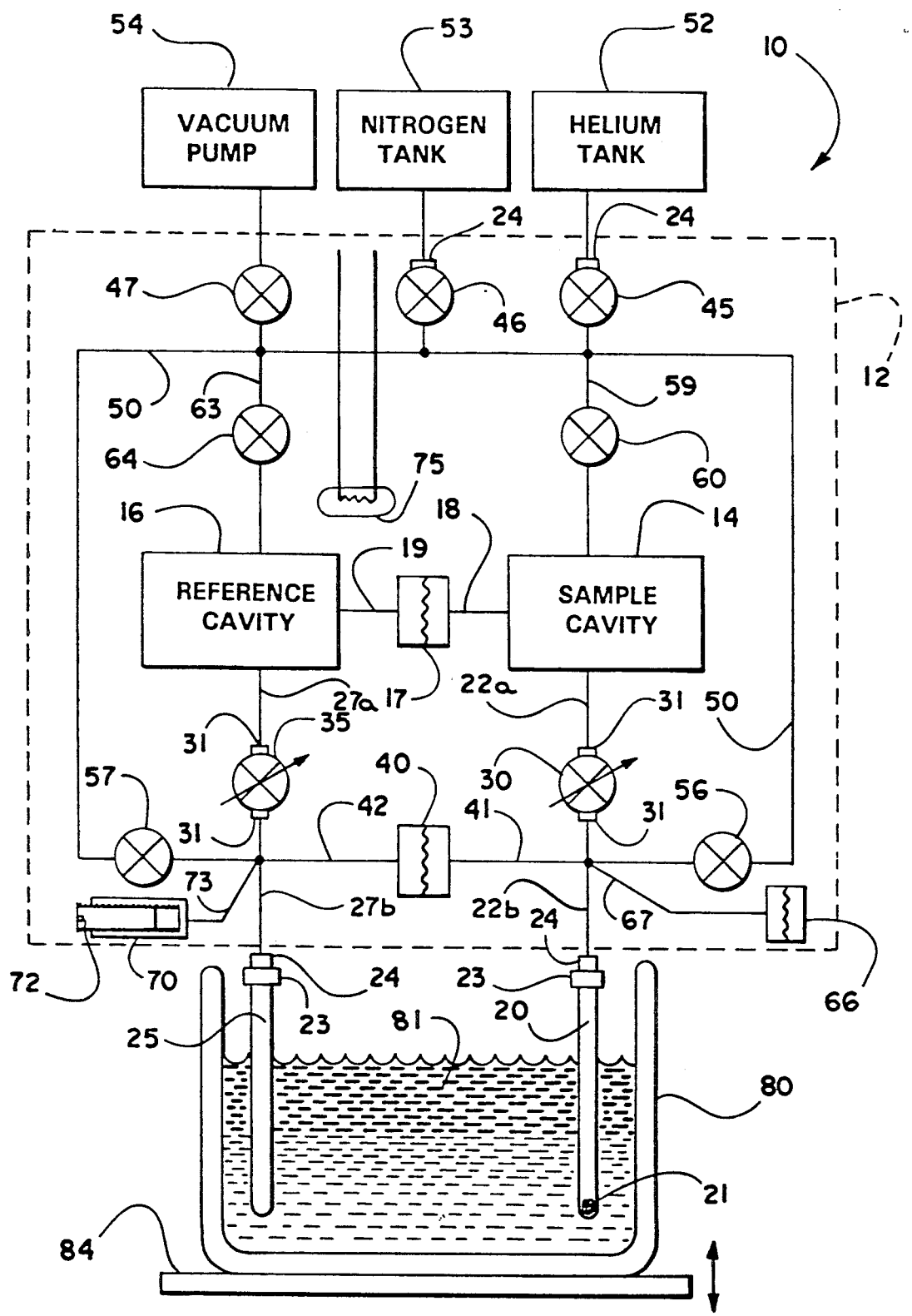
Fig_1

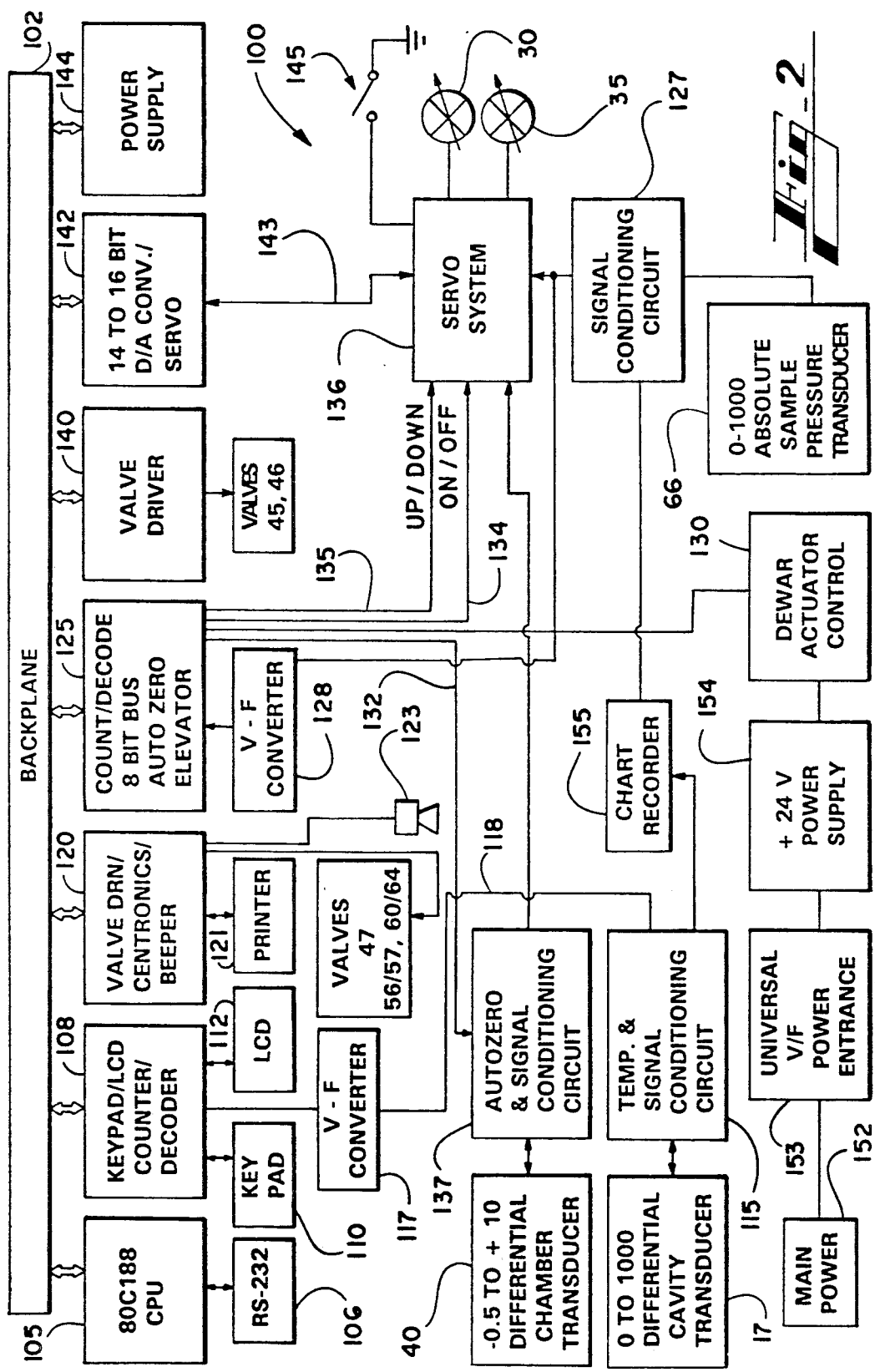

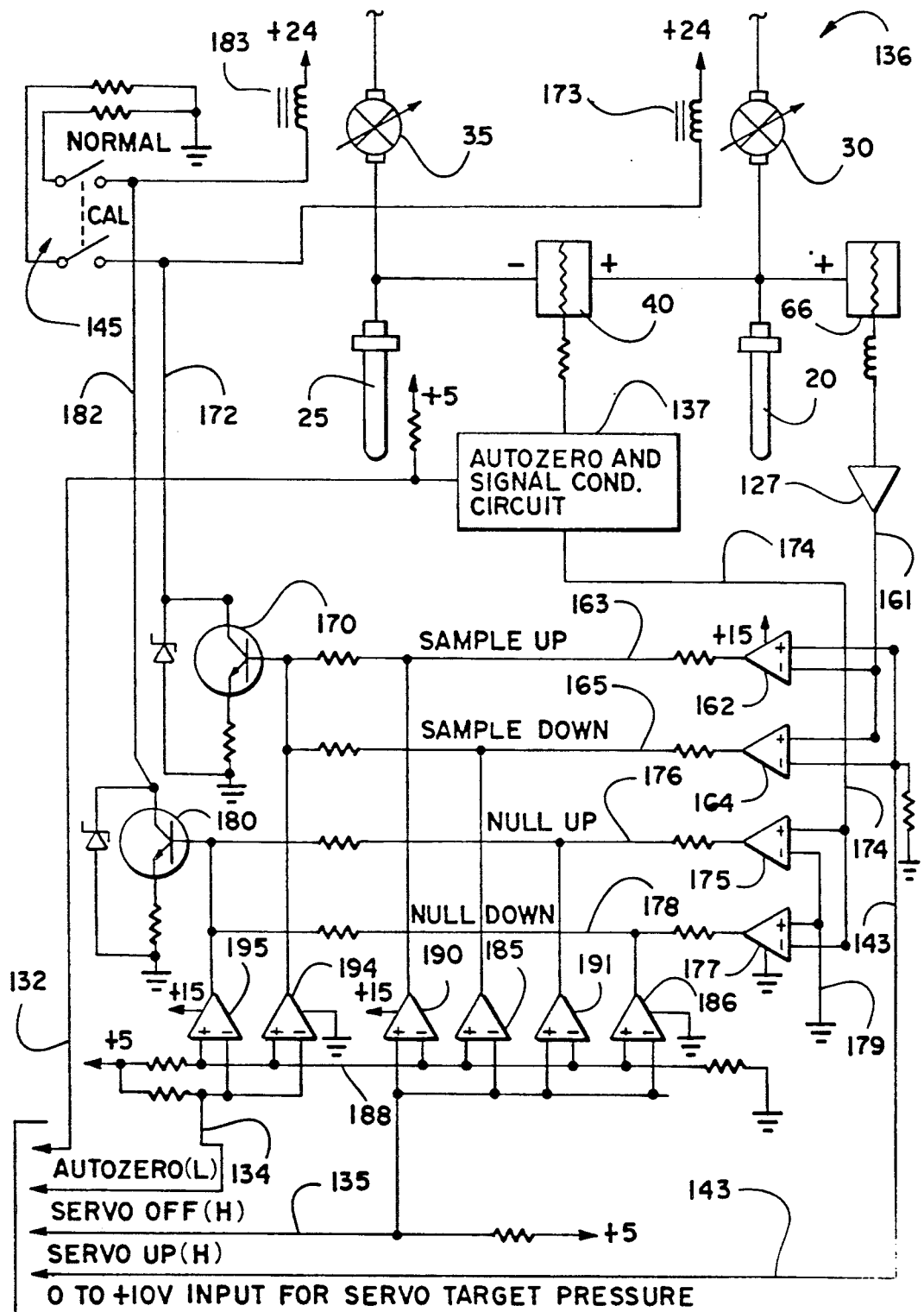
Fig_3

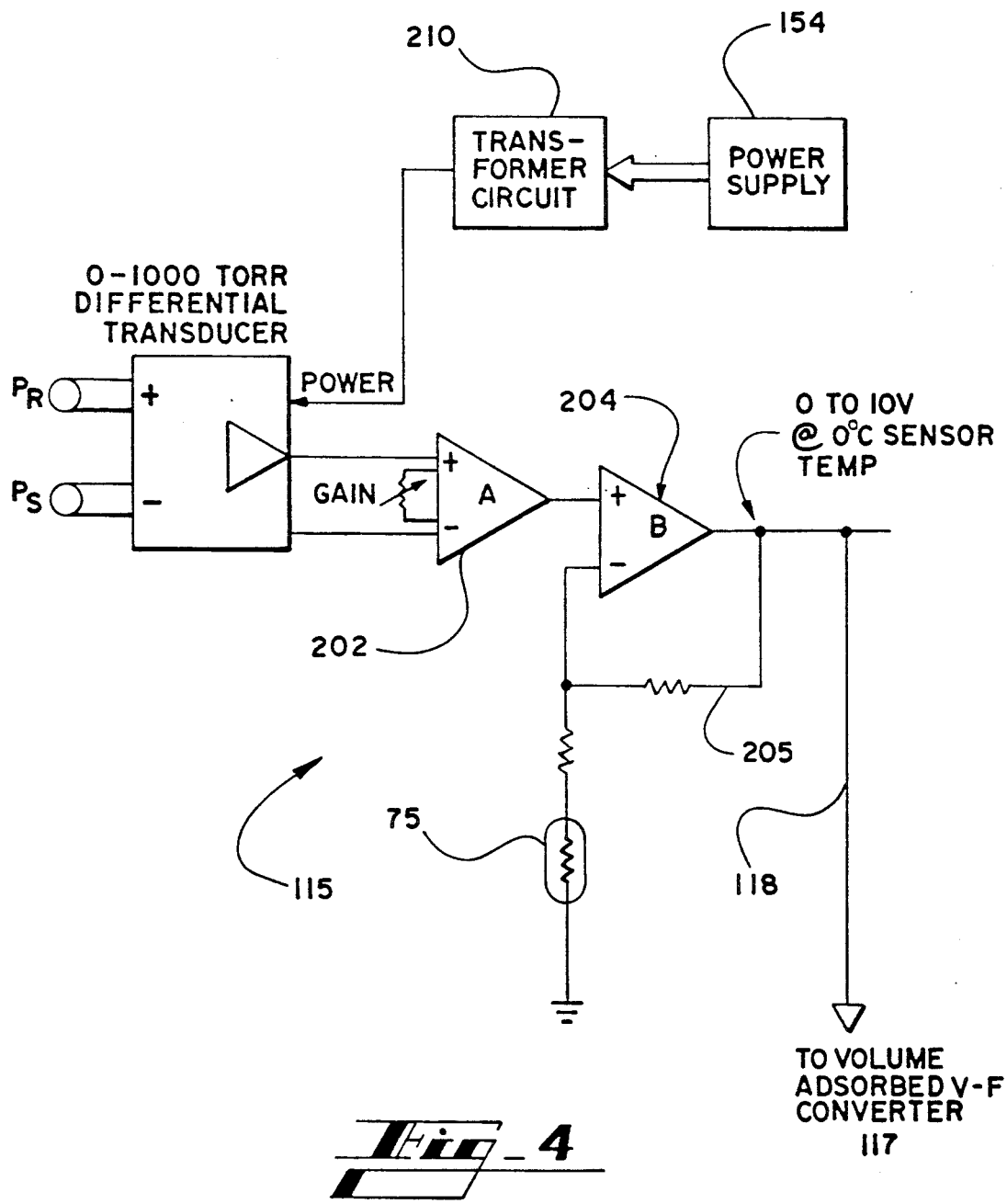
Fig_4

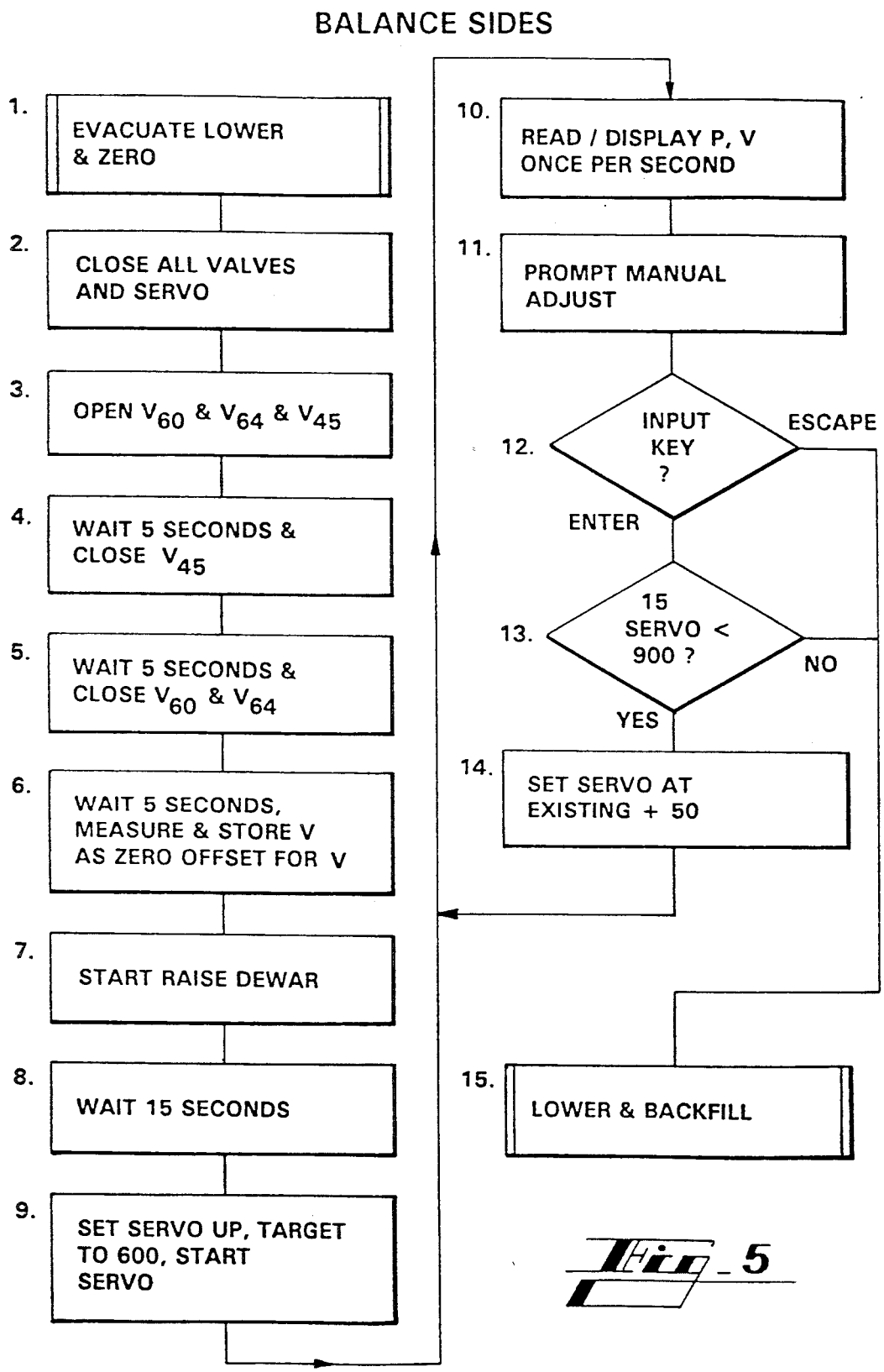
Fig_5

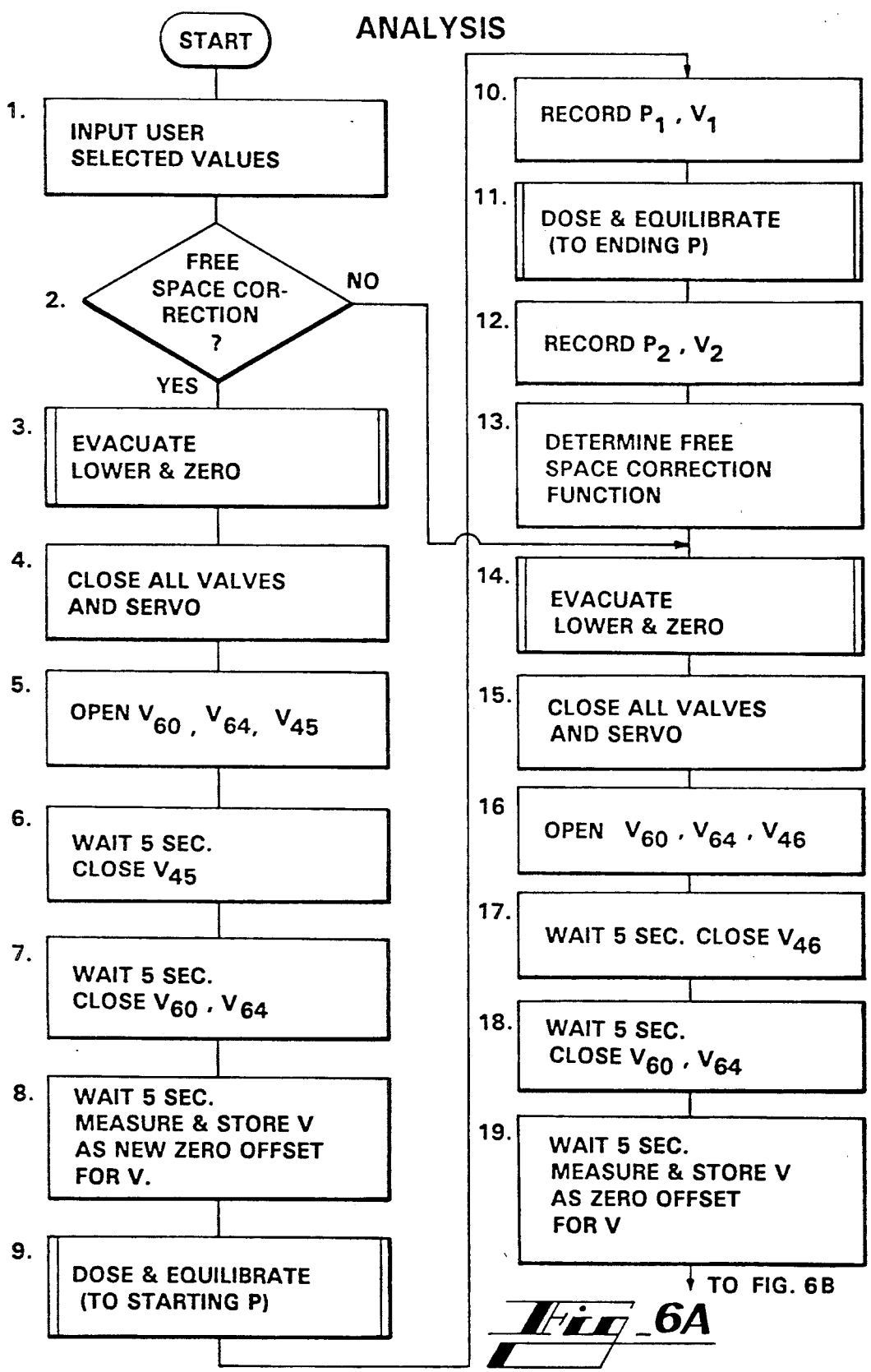
Fig_6A

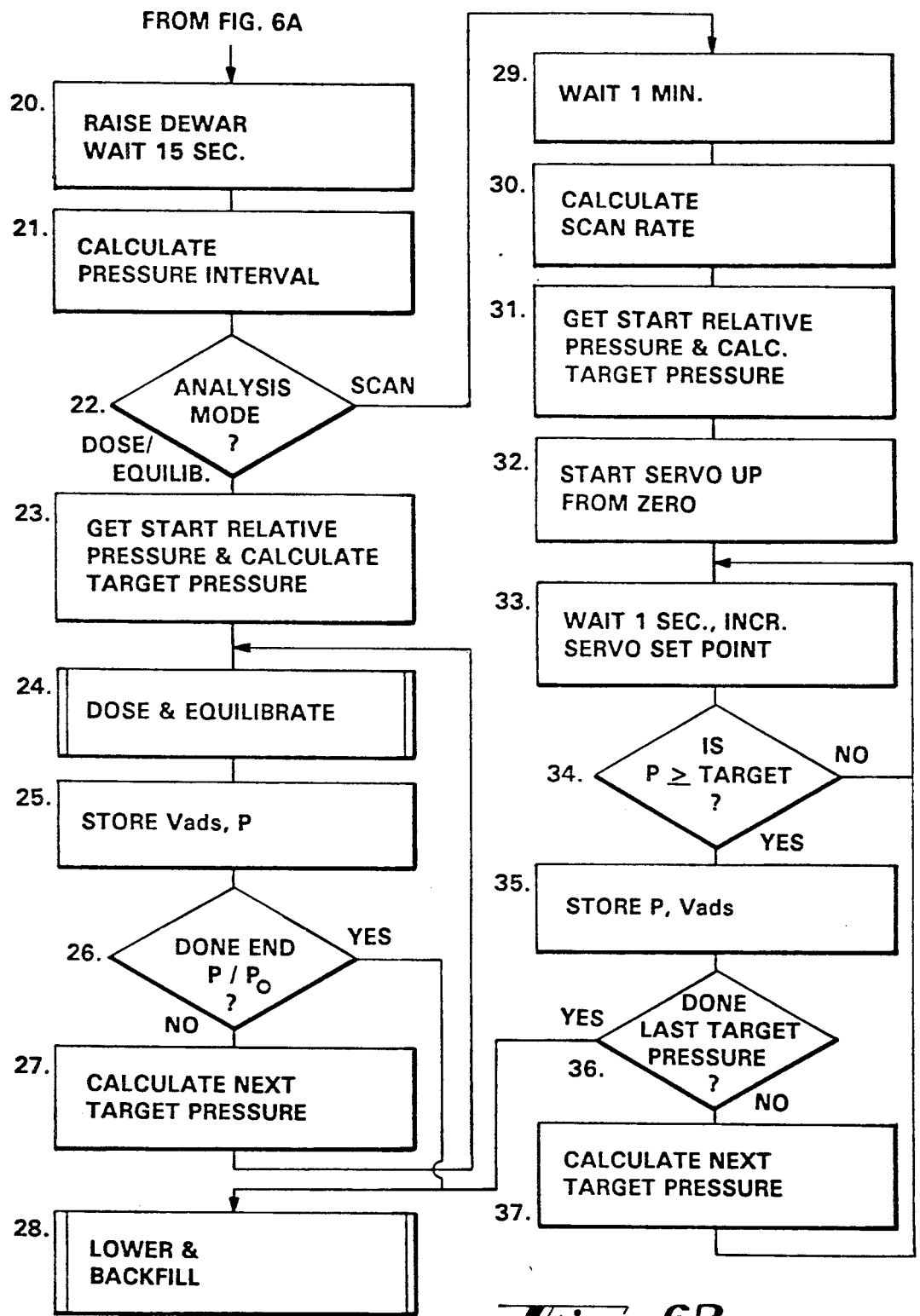
Fig_6B

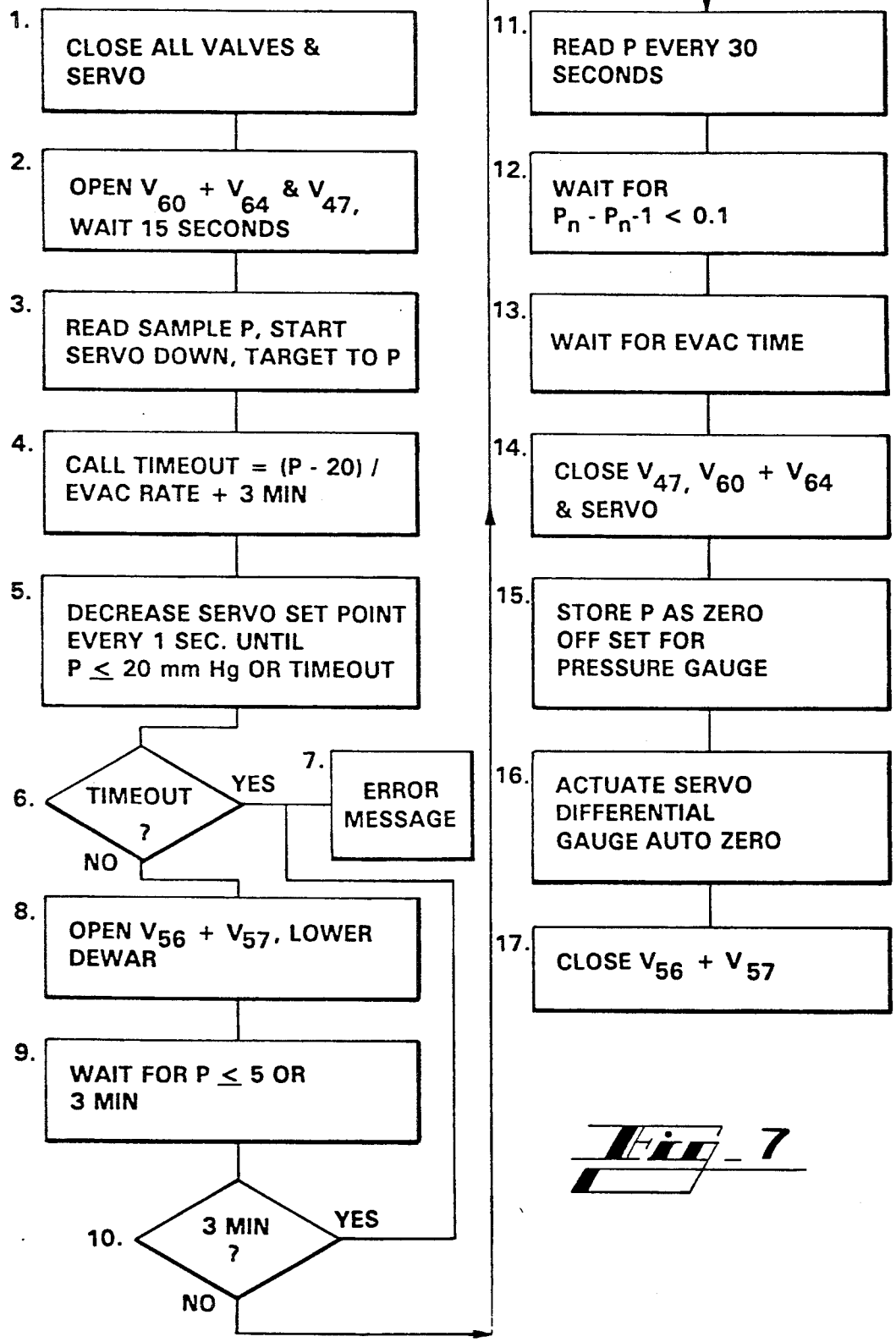
Fig_7

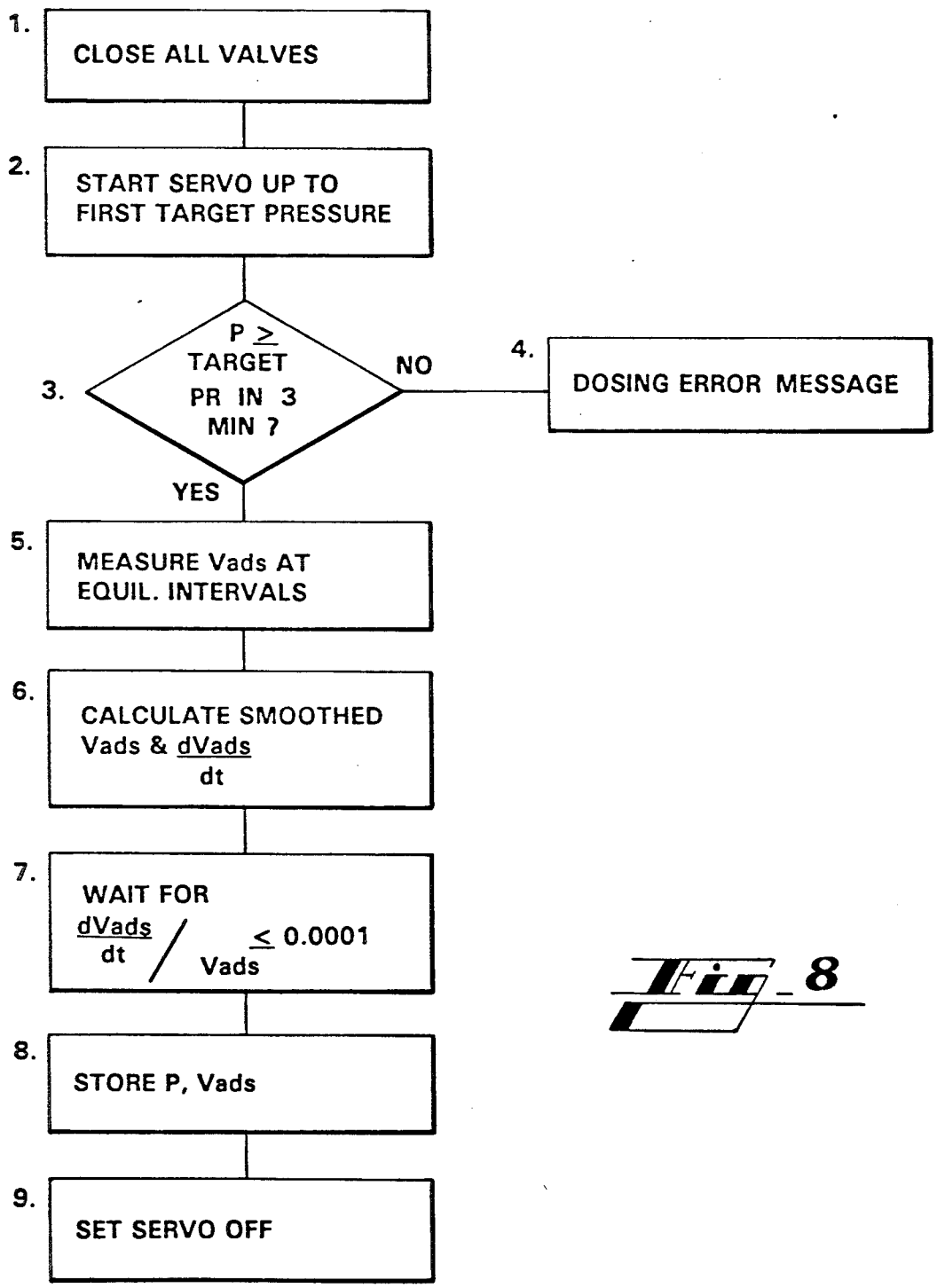
Fig_8

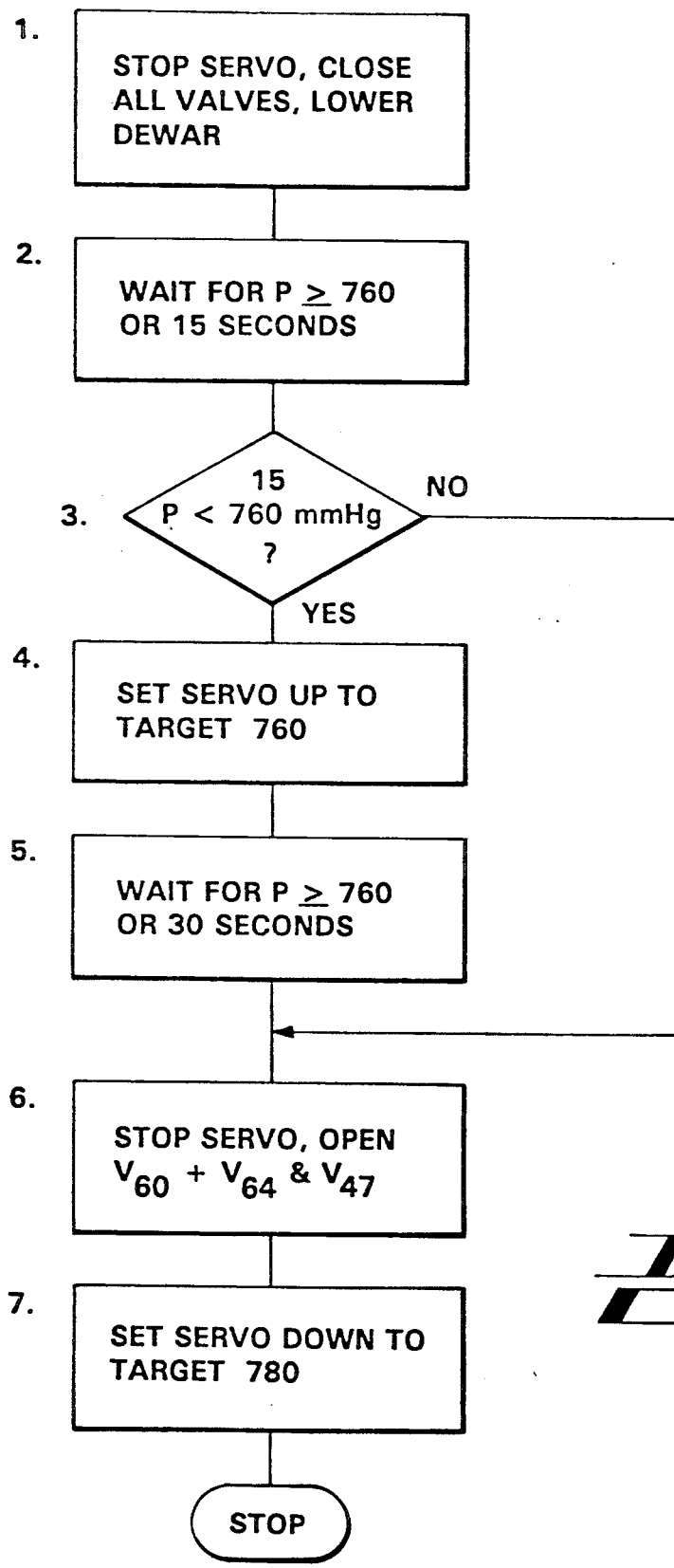
Fig_9

DYNAMICALLY BALANCED, DIFFERENTIAL GAS ADSORPTION APPARATAUS

TECHNICAL FIELD

The present invention relates to an apparatus and method for obtaining adsorption data, and more particularly relates to an apparatus and method for using the differential pressures between a pair of dosing systems, one including a sample chamber and the other including a null chamber, to indicate the amount of gas adsorbed by the sample.

BACKGROUND ART

Powders consisting of nonporous particles as well as small, granular, and porous materials of a variety of types are utilized in huge amounts by modern industry. The extent of their surface area and the size and magnitude of the pores they contain is of great significance in the way powders behave. Some powdered materials, carbon black, for example, exhibit an extremely high surface area even in small quantities. The pores in powdered catalysts, particularly zeolitic ones, can be as small as a few angstroms in diameter and nearly all of one size. Carbon black surface area per unit mass is critical in formulating rubber for long-life automobile tires, and zeolite pore size is a determining factor in which chemical reaction is promoted by a zeolite catalyst. Other examples of the critical importance of surface structure are to be found in the rate at which pharmaceutical tablets dissolve, the fusion and resulting density of ceramic bodies, and the conductance of electrical resistors.

Surface area is established by following, basically, the so-called BET technique (Brunauer, S., Emmett, P., and Teller, E., "The Adsorption of Gases in Multimolecular Layers," *J. Am. Chem. Soc.* 60, 309–19 (1938)), wherein a gas is adsorbed at a constant low temperature, ordinarily the temperature of liquid nitrogen, on the surface of the solid to an amount described by the well known BET equation as a monomolecular layer. The size of the gas molecule and the amount of gas, hence number of gas molecules, then establishes the magnitude of the surface. Mesopore and macropore sizes (defined, respectively, as greater than 20 Å and 500 Å in diameter) and volumes are computed from data relating the quantity of gas adsorbed beyond that forming the monomolecular layer and the pressure at which the adsorption occurred in conformity with the known BJH calculation procedure (Barrett, E., Joyner, L., and Halenda, P., "The Determination of Pore Volume and Area Distribution in Porous Substances-I. Computation from Nitrogen Isotherms," *J. Am. Chem. Soc.* 73, 373–80 (1951)).

Materials having microporous characteristics (pores less than 20 Å in diameter) are evaluated in the same manner as above, that is, the materials are exposed to increasing amounts of gas and data are collected relating the quantity of gas adsorbed to the prevailing physical conditions. Extraction of material physical parameters from the data is in accordance with the known interpretation of Langmuir (*J. Am. Chem. Soc.* 38, 2219 seq. et. seq. (1916) and *J. Am. Chem. Soc.* 40, 1361 et. seq. (1918)), and the computational procedure pioneered by Polanyi (*Trans. Faraday Soc.* 28, 316 et. seq. (1932)), and expanded on by others, most notably Dubinin and Astakhov (*Adv. Chem. Ser.* 102, 69 et. seq. (1971)).

By subjecting the powdered sample to incrementally increasing volumes of gas to a point at or approaching the saturation pressure of the particular gas, an adsorption isotherm may be obtained. Reversing the procedure by subjecting the sample to incremental reductions in gas pressure, also at a constant temperature, yields a desorption isotherm. The volume of gas adsorbed per unit mass of solid depends on the equilibrium pressure of the gas, the absolute temperature, and the nature of the gas and solid. An adsorption isotherm is a plot at constant temperature of the gas adsorbed per unit mass of solid versus the relative pressure $P/P_o$, where $P_o$ is the saturation vapor pressure of the adsorbate gas. Thus, any device designed to measure surface area or pore volume data must be able to accurately determine the quantity of gas adsorbed.

Several instruments have been developed for measuring adsorption. In volumetric instruments, such as disclosed in U.S. Pat. No. 3,850,040 and U.S. Pat. No. 4,566,326, the sample is dosed with discrete amounts of an adsorbate gas from a manifold of known volume and pressure. The resulting pressure in the combined volume of the manifold and sample chamber is measured in order to determine how much of the gas is adsorbed by the sample at selected relative pressures. The volume of the manifold and of the sample compartment must be known very precisely. Thus one disadvantage of this system is that the free space, the volume within the sample compartment not occupied by the sample, must be determined precisely, because the volume of the sample varies with the quantity of sample that is chosen for analysis. Free space compensation must take into account variations in free space capacity which occur as the level of liquid nitrogen coolant surrounding the sample drops, changing the temperature profile along the sample compartment. Another problem with the volumetric system is that compensation must be made for the non-ideal behavior of the adsorbate gas. Also, the accuracy of the system depends upon absolute pressure transducers having a relatively wide pressure range. The manner of use of such transducers to determine gas volumes adsorbed requires determining the differences between two closely spaced pressures, causing effective errors and noise to increase significantly. Thus, expensive transducers with very tight noise, linearity, and error specifications must be used. Finally, the dosing sequence is tedious and lengthy.

In flowing gas sorption analyzers, such as disclosed in U.S. Pat. No. 2,960,870 and U.S. Pat. No. 3,555,912, a mixture of adsorbate and non-adsorbing gases, such as nitrogen and helium, are continuously passed over the sample. The relative proportions of the two gases in the stream are altered in order to change their relative pressures as they pass over the sample, which alters the amount of the adsorbate that will be adsorbed by the sample. Thermal conductivity detectors are placed before and after the sample to measure the change in composition of the gas stream caused by the sample, and thereby to obtain an indication of adsorption by the sample. One disadvantage of the flowing gas system is that the mixing of helium with the adsorbate limits the rate at which the adsorbate can be delivered to the sample for adsorption, and therefore slows the analysis. Also, measurements are taken at only one relative pressure of the adsorbate, with the mixture at atmospheric pressure, and the detectors are at room temperature.

Therefore, the saturation pressure of the adsorbate during the run may vary with ambient conditions and is generally not accurately known. Finally, samples adsorbing large amounts of gas may require as long as 25-50 minutes to equlibrate after changes in the gas mixture, especially at low relative pressures.

A third prior system, disclosed in U.S. Pat. No. 4,762,010, delivers gas to the sample continuously at a rate claimed to be less than the equilibrium rate of adsorption with respect to the sample. The gas is released from a bulb of known volume through a leak valve into a sample compartment of known free space, and the pressure within the supply bulb and the sample compartment are both measured repetitively. The change in pressure in the bulb provides an indication of the amount of gas admitted to the sample compartment, which together with the change in pressure in the sample compartment can be used to provide an indication of the amount of gas adsorbed by the sample. Points on the adsorption isotherm can be determined continually. Problems include the slow dosing rate, the requirement for accurate knowledge of and compensation for the free space, and use of wide range absolute pressure transducers, as discussed above.

Some sorption analyzers have utilized differential pressure measurements to measure adsorption effects. For example, in the flowing gas analyzers discussed above, the difference in relative pressures of the two gases is measured by a Wheatstone bridge connecting two thermal conductivity detectors.

U.S. Pat. No. 3,349,625 discloses a gas chemisorption instrument consisting of two systems of constant and known volume, each having a reservoir of known volume, a sample chamber of known volume, valved tubing between the reservoir and chamber, and an absolute pressure measuring device attached to each reservoir. A differential pressure-measuring device is connected to measure the difference in pressure between the systems. One sample chamber contains a chemisorbing sample and the other contains a non-chemisorbing or physically adsorbing sample. The differential pressure at chemisorbing conditions is said to indicate the amount of gas chemisorbed by the chemisorbing sample.

A surface area measuring device marketed by Strohlein GmbH & Co. under the mark "AREA-meter" fills sample and comparison vessels of equal volume with nitrogen at the same pressure and ambient temperature. When brought to liquid nitrogen temperature, adsorption in the sample vessel creates a difference in pressure in the two vessels, which is measured on a differential manometer. The amount of nitrogen adsorbed by the sample can be calculated from the pressure difference and the filling pressure. U.S. Pat. No. 3,059,478 discloses a sorption system which uses a differential pressure gauge to obtain the differential pressure between a sample tube and a reference tube which appears to contain a fixed amount of nitrogen gas. A manometer system is used to supply fixed mass doses of nitrogen to the sample tube, and a plot of mass introduced to the sample versus the differential pressure is generated. This system relies on being able to deliver a sequence of precisely equal doses, and does not overcome all of the problems in the art discussed above.

Thus, there has been a need in the art for a sorption analyzer which is capable of providing precise data on the volume of gas adsorbed by a sample, is not limited in speed by the structure or operation of the apparatus, does not rely for accuracy on readings of closely spaced pressures by wide range absolute pressure transducers, does not require determination of or temperature compensation for free space in a sample compartment, and does not require compensation for non-ideal behavior of the adsorbate gas.

SUMMARY OF THE INVENTION

The present invention solves the above-described problems in the art by providing a method and apparatus for sorption analysis which, when optimally practised, is limited in dosing speed only by the ability of the sample to adsorb the adsorbate gas, uses differential pressure transducers operating within their optimal range to obtain adsorption data, can operate without a determination of the free space in a sample chamber, and is unaffected by non-ideal gas behavior or temperature changes of connecting passageways resulting from the evaporation of sample chamber coolant. The system doses a sample chamber and a null chamber from essentially equal volumes of gas, and causes the chambers to be dosed such that any pressure difference between them, caused by adsorption, is eliminated. The differential pressure between the essentially equal volumes of gas then indicates the amount of gas adsorbed by the sample.

Generally described, the present invention provides a method and apparatus for obtaining adsorption data, by filling a first cavity and a second cavity with an adsorbing gas to the same pressure, the temperature in said first cavity being essentially equal to the temperature in said second cavity; admitting the gas from the first cavity into a first chamber; admitting the gas from the second cavity into a second chamber, one of the first or second chambers containing a sample capable of adsorbing the gas, and the temperature in said first chamber being essentially equal to the temperature in said second chamber; adjusting the amount of the gas admitted into the chambers until the pressure difference between the chambers is essentially eliminated; and measuring the pressure difference between the first and second cavities.

As long as the ratio of the volume of the cavity from which gas is dosed into the sample-containing chamber to the volume of the sample-containing chamber is equal to the ratio of the volume of the other cavity to the volume of the other chamber, only the volume of the cavity from which gas is dosed into the sample-containing chamber need be known accurately. Preferably, the volumes of the first and second cavities are essentially equal, and the volumes of the two chambers are essentially equal, to simplify the calculations for determining the volume adsorbed. In the preferred embodiment, the volumes of the two sides of the instrument may be equalized by admitting a non-adsorbing gas into the instrument; and adjusting the volume of either side until the pressure difference between them is essentially eliminated. More particularly described, this is preferably accomplished by filling the first and second cavities with a non-adsorbing gas to the same pressure; connecting the first cavity to the sample chamber and the second cavity to the null chamber; and adjusting the volume of the null chamber until there is no pressure difference between the sample chamber and the null chamber. This balancing procedure may be performed with both chambers empty, or with the sample in place. In the former case, the effect of sample volume can by ignored for very small samples, or can be taken into account either by a mathematical free space compensation or by placing inert, non-adsorbing, glass beads or the like in the null chamber. In the latter case, the balancing will eliminate any free space error for the particular sample being analyzed.

The temperature within each of the two cavities should remain essentially equal to the temperature in the other cavity during the analysis, although the temperature need not remain precisely constant over time. The chambers must be at a temperature at which adsorption can occur during the analysis, which typically, as in the case of nitrogen gas, requires immersion in a cryogenic bath. The temperature at the location of the sample in the sample chamber should remain essentially equal to the corresponding location in the null chamber, and the temperature profiles along the two chambers should be the same for accurate results. Again, the values of the two essentially equal temperatures at any point along the profiles need not remain precisely constant over time.

The apparatus and method can be operated to dose the chambers either continuously or in discrete amounts. Data can be obtained for selected target relative pressures. If dosing is continuous and at a rate close to the equilibrium rate of adsorption of the sample, an adsorption isotherm can be plotted as the analysis proceeds. Single point BET analyses can be obtained as fast as the sample can adsorb the adsorbate gas.

In the preferred embodiment, a feedback system is used to eliminate the pressure difference between the sample and null chambers. Either one of the chambers can be dosed with adsorbate gas, either continuously or incrementally, and the feedback system will automatically dose the other chamber until the differential pressure between the chambers is zero within the accuracy of the differential pressure measuring device. Since the sample is adsorbing part of the gas admitted into the sample chamber, more gas will be required from the first cavity to establish zero pressure differential between the chambers.

The invention can be used to obtain desorption data by continuing to admit the gas into the sample chamber from the first cavity until the sample is essentially saturated; isolating and evacuating the first and second cavities; admitting desorbed gas from one of the chambers into its associated cavity; admitting gas from the other chamber into the other cavity until the pressure difference between the sample chamber and the null chamber is essentially eliminated; and measuring the pressure difference between the first and second cavities.

More particularly described, the invention provides an apparatus for obtaining adsorption data, comprising means for defining a first cavity and a second cavity having essentially equal volumes, the temperature in said first cavity being essentially equal to the temperature in said second cavity; a source of adsorbing gas; fill valve means for admitting the adsorbing gas from the source into the cavities and for connecting or isolating the cavities to or from one another; a sample chamber containing a sample capable of adsorbing the adsorbing gas; a sample conduit connecting the first cavity to the sample chamber, the sample conduit including a sample dosing valve; a null chamber; a null-side conduit connecting the second cavity to the null chamber, the null-side conduit including a null-side dosing valve; the sample and null chambers being selectively positionable in a liquid bath at a temperature at which adsorption of the gas occurs; a first differential pressure transducer positioned to measure the difference in pressure between the first and second cavities; a second differential pressure transducer positioned to measure the difference in pressure between the sample chamber and the null chamber; an absolute pressure transducer positioned to measure the pressure in the sample chamber; and means for evacuating the apparatus. Preferably, the apparatus also comprises control means for operating the evacuating means to evacuate the apparatus; operating the fill valve means to fill the first and second cavities with the adsorbing gas to the same pressure and then to isolate the cavities from one another; operating the sample dosing valve to admit the gas into the sample chamber; operating the null-side dosing valve to admit the gas into the null chamber until the output of the second differential pressure transducer is essentially zero; and reading the output of the first differential pressure transducer.

The volume adsorbed is related to the output of the first differential pressure transducer between the cavities as follows:

$$V_{ads} = [P_{NC}V_{NC}/T_{NC} - P_{SC}V_{SC}/T_{SC}] * K$$

where $P_{NC}$ is the pressure within the null-side cavity, $V_{NC}$ is the volume of the null-side cavity, $T_{NC}$ is the temperature in the null-side cavity, $P_{SC}$ is the pressure within the sample-side cavity, $V_{SC}$ is the volume of the sample-side cavity, $T_{SC}$ is the temperature in the sample-side cavity, and K is a conversion factor from moles of gas to cm$^3$ at standard temperature and pressure (STP). Since the cavities are preferably made to have essentially equal volumes, and their temperatures are preferably effectively equal as a result of their proximity within a block of high thermal conductivity, $V_{NC} = V_{SC}$ and $T_{NC} = T_{SC}$. The temperature relationship could also be maintained with a conventional automatic temperature control mechanism, using a thermostat. Therefore, the volume adsorbed can be stated more simply as:

$$V_{ads} = (V/T) * \Delta P * K$$

where $\Delta P$ is the differential pressure between the cavities.

Preliminary testing has indicated that an analyzer embodying the invention can conduct an analysis for a five point BET isotherm in less than ten minutes, whereas the same analysis would have taken about one hour using widely accepted conventional equipment. Furthermore, the reproducibility of results appears to be about one part in 500, or about 0.2%.

Thus, it an object of the present invention to provide an improved apparatus and method for obtaining sorption data.

It is a further object of the present invention to provide an apparatus and method for obtaining sorption data that is not limited in speed by the structure or operation of the apparatus or by the slowness of changing gas mixtures.

It is a further object of the present invention to provide an apparatus and method for obtaining sorption data that does not rely for accuracy on readings of closely spaced pressures by wide range absolute pressure transducers.

It is a further object of the present invention to provide an apparatus and method for obtaining sorption data that does not require determination of or temperature compensation for free space in a sample compartment.

It is a further object of the present invention to provide an apparatus and method for obtaining sorption data that does not require detection and correction for non-ideal behavior of the adsorbate gas.

It is a further object of the present invention to provide an apparatus and method for obtaining sorption data capable of performing single point, multiple point, and scanning type analyses.

It is a further object of the present invention to provide an apparatus and method for obtaining sorption data capable of performing accurate analyses of very low surface area samples.

Other objects, features and advantages of the present invention will become apparent upon review of the following description of embodiments of the invention and the appended drawing.

BRIEF DESCRIPTION OF THE DRAWING

FIG. 1 is a schematic diagram of a sorption analyzer embodying the present invention.

FIG. 2 is a block diagram showing the electronics system for controlling the analyzer of FIG. 1.

FIG. 3 is a schematic diagram showing in detail the servo control circuit of FIG. 2.

FIG. 4 is a schematic diagram showing in detail the signal conditioning circuit of FIG. 2 for the output of the volume adsorbed differential transducer.

FIG. 5 is a logic flow diagram for the routine used in connection with balancing the volumes of the two sides of the analyzer of FIG. 1.

FIGS. 6A and 6B are logic flow diagrams for the analysis routine utilized in operation of the analyzer of FIG. 1.

FIG. 7 is a logic flow diagram for the subroutine of FIG. 6 used to evacuate the system, lower the liquid nitrogen Dewar, and zero the volume adsorbed transducer.

FIG. 8 is a logic flow diagram for the subroutine of FIG. 6 used to dose a sample.

FIG. 9 is a logic flow diagram for the subroutine of FIG. 6 used to terminate analysis.

DETAILED DESCRIPTION

Referring now to the drawing, in which like numerals refer to like parts throughout the several views, FIG. 1 shows a schematic representation of a sorption analyzer 10 embodying the present invention. The parts of the analyzer 10 are placed, as far as possible, within or directly adjacent to a block 12 formed of a material of high thermal conductivity, such as aluminum. Furthermore, the lines and passageways to be described between such parts are preferably formed within the block whenever possible, and when not possible or not practical, are formed of stainless steel tubing.

Within the block 12, a first cavity 14 and a second cavity 16 are defined in close proximity to one another, preferably by boring with a precision drill into the block. The cavities 14 and 16, with the passageways which connect them to nearby valves, are preferably formed to have equal volumes to a high degree of accuracy, for reasons to be explained below. It has been found that a useful range of samples may be analyzed efficiently if each of the cavities is about 125–150 cm$^3$ in volume, although the cavity size may be varied as desired. The cavities and gas within them stay at essentially equal temperature as a result of the proximity of the cavities and the high thermal conductivity of the block 12.

One side of a cavity differential pressure transducer 17 is connected to the first cavity 14 by a line 18 and the other side of the transducer 17 is connected by a line 19 to the second cavity 16. Thus, the transducer 17 provides an output signal representing the difference in pressure between the cavities 14 and 16. The cavity differential pressure transducer 17 preferably has a range of 0–1000 mmHg pressure difference, accurate to within 0.5% of reading after zeroing. Noise and stability levels should permit resolution to one part in 20,000 of full scale using a ½ second integration interval. A variable reluctance differential transducer suitable for the purpose is Model DP-290-1000, manufactured by Validyne Incorporated.

A removable sample chamber or tube 20 is connected to the first cavity 14 by a line 22, which terminates in a standard Cajon type connector 23 using a polybutadiene nitrile rubber (Buna-N) O-ring (not shown). A sample 21, such as a powder, may be placed in the sample tube 20 after preparation as described below. A replaceable 2-10 micron frit 24 is provided at the end of the line 22 to protect the instrument from possible entry of particulate from the sample tube. In parallel to the sample side, a removable null chamber or tube 25 is connected to the second cavity 16 by a line 27, which terminates in a frit 24 and another connector 23. The null tube 25 is normally empty during analysis, or may contain inert material for volume adjustment as described below. The sample and null tubes are preferably formed of glass to have equal volumes within 0.05 cm$^3$.

A sample dosing valve 30 is connected to control flow of gas along the line 22 between the first cavity 14 and the sample tube 20. A line segment 22a connects the valve 30 to the first cavity 14, and a line segment 22b connects the valve 30 to the sample tube 20. A similar null-side dosing valve 35 is connected to the second cavity 16 and to the null tube 25 by line segments 27a and 27b, respectively. The dosing valves 30 and 35 are preferably commercially available electromagnetic or piezoelectric variable flow control valves having a leak rate against helium at one atmosphere of less than 6×10$^{-7}$ SCCM per minute. While being variable in a continuous analog manner within their flow range, they preferably should be fully closed with 0 volts applied, just cracked open at half the maximum voltage, and open to permit a flow of at least 20 SCCM per minute at maximum voltage. Both sides of each of the dosing valves 30 and 35 are protected against particulate contamination by 2-micron frit 31.

A chamber differential pressure transducer 40 is connected to measure the difference in pressure between the sample tube (and associated lines) and the null tube (and associated lines). A line 41 connects one side of the transducer 40 to the line segment 22b, and a line 42 connects the other side of the transducer to the line segment 27b. The chamber differential pressure transducer 40 preferably has a range of −0.5 to 0 to 10 mmHg pressure difference, accurate to within 0.5% of reading after zeroing. Noise and stability levels should permit resolution to one part in 20,000 of full scale using a ½ second integration interval. A variable reluctance differential transducer suitable for the purpose is Model DP-290-10, manufactured by Validyne, Incorporated.

Thus, it will be seen that the analyzer 10 includes a pair of basically identical dosing systems arranged in parallel, each consisting of a cavity or reservoir connected to a chamber by a flow control valve. One of the chambers contains the sample to be analyzed. The parallel systems have no gas flow connection while adsorption or desorption data are being measured, but are linked by differential pressure transducers, one of which measures the difference in pressure between the cavities, while the other measures the difference in pressure between the chambers. In summary, the analyzer 10 operates by admitting gas from one cavity to one of the chambers as directed by the operator, and causing gas to be admitted from the other cavity to the other chamber in a quantity sufficient to essentially equalize the pressures within the chambers. The differential pressure measurement between the cavities is then an indication of the amount of gas adsorbed by the sample. The process can be reversed to withdraw gas from the chambers to obtain desorption data. Although in the preferred embodiment being described, the sample chamber is dosed and the null chamber is equalized, the same data can be obtained by initially dosing the null chamber and equalizing the sample chamber.

Although as noted the parallel systems are isolated during analysis, the analyzer 10 includes other elements for the purpose of evacuating the systems and filling them with one or more gases as required. A common line 50 extends between the line segments 22b and 27b and provides a convenient vehicle for interconnection of such other elements. Gas may be supplied from a helium tank 52 to the line 50 through a valve 45, or from a nitrogen tank 53 through a valve 46. Each of the valves 45 and 46 is protected by a 2-10 micron frit 24 on the tank side of the valve. The valves 45 and 46 may be non-heating magnetically latching solenoid valves of the type sold under the trademark Magnelatch by Skinner-Honeywell, or Clippard solenoid valves of the type which require only a low level of continuous power. Clippard valves are closed in a power-off state, and are operated only for a few seconds to perform the tasks of valves 45 and 46, so there is no significant time for heating of the apparatus to occur. A vacuum pump 54 is connected to the line 50 through a Magnelatch valve 47.

The sample cavity 14 is connected to the common line 50 by a line 59 containing a Magnelatch valve 60. Similarly, the null cavity 16 is connected to the common line 50 by a line 63 containing a Magnelatch valve 64. The valves 60 and 64 are operated simultaneously by the same current pulse provided by the control circuit to be described below. The common line 50 also contains a sample evacuation/isolation valve 56 positioned adjacent to the line segment 22b, and a null-side evacuation/isolation valve 57 positioned adjacent to the line segment 27b. The valves 56 and 57 are of the Magnelatch type, and are operated simultaneously by the same current pulse provided by the control circuit. Simultaneous operation of the valve pairs as just described prevents the transducers 17 and 40 from being subjected to large pressure differences which might damage them. It will be understood that the branches of the line 50 to the vacuum pump 54 from the valves 56/57 can be joined near the valves rather than running separately to the pump as shown.

An absolute pressure transducer 66 is connected to the line segment 22b by a line 67. The transducer 66 preferably has a full scale range of 0–1000 mmHg, is accurate to within 0.5% after zeroing, and has an internal volume not to exceed 1.5 cm$^3$. Noise and stability levels should permit resolution of 0.1 mmHg over a ½ second integration interval.

A volume compensation adjustment used to balance the volumes of the sample and null sides is provided by a volume adjustment cylinder 70 containing a variable position piston 72. The cylinder 70 is connected to the line segment 27b by a line 73, and can be adjustable either manually, such as using a screwdriver, or automatically under computer control. A procedure for manual balancing is described below.

The temperature within the block 12 is monitored by a temperature sensor 75 positioned in the block adjacent to the cavities 14 and 16. This sensor is preferably a platinum resistance-temperature-detector (RTD), which can be configured to provide a highly accurate increase in resistance proportional to increase in the surrounding temperature. As described below, the signal from this sensor is used to provide temperature compensation for the output signal of the cavity differential transducer 17.

The sample and null tubes 20 and 25 are brought to the temperature at which adsorption of nitrogen occurs by immersing them in a Dewar 80 containing liquid nitrogen 81. To promote temperature uniformity, the tubes optionally may be fitted with sleeves of the type described in U.S. Pat. No. 4,693,124. A conventional elevator 84 is provided to raise and lower the Dewar 80 as required during the analysis.

Electronic Controller

The apparatus shown in FIG. 1 may be operated by a computer controlled electronic circuit 100 shown in an overall block diagram in FIG. 2. The controller 100 may be conventionally arranged with a plurality of printed circuit boards (PCB's) engaged in slots in a backplane PCB 102. The backplane carries necessary STD Bus and input/output signals required to interface between the other PCB's. A central processing unit (CPU) card 105 is plugged into the backplane, and is preferably a VersaLogic VL-188-1 card carrying an 80C188, 5 MHz programmable microprocessor. The card 105 also provides a conventional RS-232 interface 106 for exporting data to other devices.

An adsorption/keypad/LCD PCB 108 is also plugged into the backplane. The PCB 108 receives input signals from a 16 key keypad 110 provided for operator entry of run conditions and numerical data, and provides output to a 2×20 character liquid crystal display (LCD) 112, which displays run time information, sample status, and analysis results. The PCB 108 also receives a frequency signal from a voltage-to-frequency converter 117, representing a volume adsorbed signal from the cavity differential pressure transducer 17. After signal conditioning and temperature compensation by a circuit 115, shown in detail in FIG. 4, the analog signal from the transducer 17 is transmitted along line 118 to the voltage-to-frequency converter 117, and may be displayed on the LCD 112. The PCB 108 preferably contains debouncing, decoding and latching circuits for the keypad 110, data drivers, control and counting of the voltage-to-frequency converter output, and address decoding circuits.

A valve driver/printer/beeper PCB 120 is also plugged into the backplane 102. The PCB 120 is connected to a printer 121, a beeper 123 for sounding warning tones to the operator, and the Magnelatch valves 47, 56/57, and 60/64. It carries current sinks and power down closure circuits for these valves, and a Centronics parallel printer port and status latch.

A pressure/autozero/elevator PCB 125 is also plugged into the backplane 102. The PCB 125 receives a frequency signal from a voltage-to-frequency converter 128, representing an absolute pressure signal from the absolute pressure transducer 66. After signal conditioning by a circuit 127, also shown in FIG. 3, the analog signal from the transducer 66 is transmitted to the voltage-to-frequency converter 128, and on to the PCB 125, where the signal is controlled and counted. The PCB 125 also contains circuitry to drive the elevator 84 between two positions, up or down, and allow software to read its current state. This control signal is transmitted along a line 129 to an elevator motor (not shown) and via an associated elevator actuator circuit 130. Two limit switches (not shown) sense when the elevator is in the full up or full down position and remove power from the elevator motor when the limit switches are reached.

The PCB 125 also contains circuitry for initiating autozeroing of the chamber differential transducer 40 by an autozero and signal conditioning circuit 137 which receives the output of the transducer 40. The initiating signal is transmitted along line 132. The output of the circuit 137 is directed to a servo system circuit 136 which drives the flow control valves 30 and 35, and is shown in detail in FIG. 3. Other inputs to the servo system circuit 136 directly from the PCB 125 include commands along line 134 to turn the servo system on or off and along line 135 to set the mode of the servo system to "up" (for adsorption) or "down" (for desorption). A valve driver PCB 140 is also plugged into the backplane 102, and carries circuitry for driving the Clippard valves 45 and 46.

A target pressure PCB 142 is also plugged into the backplane 102. The PCB 142 carries a 16 bit digital-to-analog converter for providing analog pressure set point signals along a line 143 to the servo system 136. These signals are based on target pressure levels and run parameters from the operator via the software, for use in dosing the sample.

Finally, a power supply PCB 144 is connected to the backplane to provide power for the electronics. Power for the valves, transducers, and elevator is taken from the local power main 152 and passed through an EMI filtered, fused, multi-voltage selectable, IEC compatible CORCOM power entry module 153, and a DC power supply module 154 supplying output voltages as required for the components, from −15 VDC to +24 VDC.

The analog output of the conditioning circuit 115, representing volume of gas adsorbed, may also be directed to the Y axis of an X-Y chart recorder 155 for plotting isotherms. The X axis input is the output of the absolute pressure transducer 66 via the conditioning circuit 127.

The servo system controller circuit 136 is shown in more detail in FIG. 3. The conditioning circuit 127 includes an amplifier which converts the 0–1000 mmHg output signal of the absolute pressure transducer 66 to 0–10 volts. This signal is transmitted along line 161 to the negative input of an operational amplifier 162 and to the positive input of an operational amplifier 164. The remaining inputs of these two amplifiers 162 and 164 are connected to the set point pressure signal coming from the PCB 142 along line 143. The operational amplifier 162 is selected such that if during adsorption the target pressure is greater than the actual pressure, the difference is converted into a positive voltage along line 163. Conversely, if during desorption the target pressure is less than the actual pressure, the difference is converted by the amplifier 164 into a positive voltage along line 165. Both lines 163 and 165 are connected to a transistor 170, which when activated causes an operating voltage to pass along a line 172 to a driving coil 173 of the sample flow control valve 30. Opening of the valve 30 allows gas to pass into or out from the sample tube 20, depending on whether adsorption or desorption is currently in progress.

Similarly, operational amplifiers 175 and 177 are provided for driving the null-side flow control valve 35. The output of the chamber differential pressure transducer 40 passes to the autozero and conditioning circuit 137, which may be a commercially available circuit, for example Analog Devices chip No. AD7569. An amplifier within the conditioning circuit converts the −0.5 to 10 mmHg output of the transducer 40 into a −0.5 to 10 volt signal. The circuit 137 also applies a correcting voltage to the output of the transducer 40 if the output is not 0 under conditions of vacuum across both sides of the transducer 40. The correcting voltage is reset only via the software, described below, when vacuum has been drawn on both sides of the transducer.

The corrected output from the transducer 40 is directed along a line 174 to the positive input of the amplifier 175 and to the negative input of the amplifier 177. The other inputs of these amplifiers are grounded. The operational amplifier 175 is selected such that if during adsorption the differential pressure between the chambers is greater than 0, that is, if the sample pressure is greater than the null-side pressure, the difference is converted into a positive voltage along a line 176. Conversely, if during desorption the differential pressure between the chambers is less than 0, that is, if the null-side pressure is greater than the sample pressure, the difference is converted by the amplifier 177 into a positive voltage along a line 178. Both lines 176 and 178 are connected to a transistor 180 to cause an operating voltage to pass along line 182 to a driving coil 183 of the null-side flow control valve 35. Opening of the valve 35 allows gas to pass into or out from the null tube 25, depending on whether adsorption or desorption is currently in progress.

It will be apparent from the foregoing description that the signals relating to desorption (along lines 165 and 178) should not be operative when adsorption is taking place, and conversely that the signals relating to adsorption (along lines 163 and 176) should be disabled during desorption. This is accomplished using comparators 185, 186, 190, and 191, which have open collector outputs. The outputs of comparators 185 and 186 are connected to lines 165 and 178, respectively, and the negative inputs of comparators 185 and 186 are connected to the servo up or down instruction signal on line 135 from the PCB 125. The positive inputs of comparators 185 and 186 are connected to a line 188 which is configured so that the comparators short the signals on lines 165 and 178 to ground when the servo instruction signal state is high (adsorption).

Similarly, the outputs of comparators 190 and 191 are connected to lines 163 and 176, respectively, and the positive inputs of comparators 190 and 191 are connected to the servo up or down instruction signal on line 135 from the PCB 125. The negative inputs of comparators 190 and 191 are connected to the line 188 which is configured so that the comparators short the signals on lines 163 and 176 to ground when the servo instruction signal state is low (desorption).

A similar arrangement is utilized to turn the entire servo system on or off. The on/off signal along line 134 from PCB 125 is fed to the negative inputs of a pair of comparators 194 and 195. The output of the comparator 194 is connected to lines 163 and 165 just prior to the transistor 170, and the output of the comparator 195 is connected to lines 176 and 178 just prior to the transistor 180. The positive inputs to the comparators are connected to the line 188, so that when the signal on line 134 is high, all signals from the operational amplifiers 162, 164, 175 and 177 are shorted to ground. Conversely, when the signal on line 134 is low, the servo system is operational.

The circuit 136 also includes a maintenance switch 145 which can be used to establish momentarily a threshold valve-opening current in the coils 173 and 183 prior to maintenance such as adjustment of the valves 30 and 35.

FIG. 4 shows the conditioning circuit 115 associated with the output of the cavity differential transducer 17. The output from the transducer 115 is passed through a scaling or level shifting amplifier 202, which is adjustable to convert the 0-1000 mmHg transducer range to an output signal of 0-10 volts. Since the temperature of the block 12 is not positively controlled to maintain a constant temperature, the value of the pressure difference measured by the transducer 17 will go up with an increase in temperature and down with a decrease in temperature even though no change in the quantities of gas within the cavities has occurred.

The circuit 115 compensates for any changes in temperature, so that its output measures quantity independent of the actual temperature differential. The output of the amplifier 202 goes to the positive input of a gain amplifier 204 having a negative feedback loop 205. The amplifier 204 is selected such that at 273.15° K., the gain is $(1 \times V)$, where V is the constant volume of the cavities. The temperature sensor 75 described above is connected between the feedback loop 205 and ground. Thus, a scaling factor of (273.15/T, °K.) is applied to the output of the amplifier 204, compensating for any temperature change by lowering the gain of the amplifier if the temperature rises and raising the gain of the amplifier if the temperature drops. The coefficient and circuit should be designed so that the output remains the same within 0.1%, despite temperature changes, over a temperature range of 10° C. to 35° C.

Power is supplied to the transducer 17 as required from the power supply PCB 154, modified by a conventional transformer circuit 210.

Sample Preparation

Preparation of samples for analysis involves degassing techniques well known to those skilled in the art and therefore not shown in the drawing. Clean nitrogen, helium, argon, or other suitable gas as chosen by the user is flowed at atmospheric pressure and at rates up to 50 cm³ per minute over the sample from a nozzle inserted into the opening of the sample tube 20. At the same time, the sample 21 is heated by placing the sample tube in a resistance heated mantle or block. Contaminants released at the elevated temperature are carried away by the clean gas flow, which also blankets the sample to prevent atmospheric exposure. After degassing, the sample tube is moved to a cooling zone while the blanketing clean gas flow continues. After cooling, the nozzle is withdrawn slowly and the sample tube is quickly plugged with a stopper and stored until needed for analysis.

Alternately, the heated sample can be placed under a vacuum to remove the desorbed contaminants, in a well-known manner.

Operation and Control Logic

The manner in which the analyzer 10 carries out analysis of a sample 21 will be described in connection with flow charts shown in FIGS. 5-9. It should be understood that the microprocessor described can be programmed by those of ordinary skill in the art to perform the functions represented by the flow charts.

Prior to beginning a run, the operator may choose to balance the sample and null sides of the apparatus using the volume compensator cylinder 70, either without the sample and null tubes or with the tubes connected and the sample 21 present within the sample tube 20. In the latter case, the volume occupied by the sample is accurately taken into account and no free space error will occur during the run. Alternately, stoppers may be placed in the connectors 23, so that the non-removable components below the valves 30 and 35 can be balanced for a longer term of use of the instrument. In this case, the sample volume may be ignored if the sample has a high surface area and high uptake of adsorbate, because the resulting error would be insignificant. Or, if the sample has a small surface area, its volume can be calculated from its density, and inert material such as glass beads of equal volume can be placed into the null chamber 25. A degree of free space compensation calculated by software can be selected, as explained below.

The control circuit software assists the operator in conducting manual balancing of the sample and null sides using a routine outlined in the flow chart of FIG. 5, entitled "BALANCE SIDES." This routine is performed only when requested by the operator. The first step is the execution of a subroutine shown in FIG. 7, entitled "Evacuate, Lower & Zero." In block 1 of FIG. 7, all valves are closed including the flow control valves 30 and 35. Then the valve pair 60/64 and the vacuum pump valve 47 are opened to lower the pressure in the cavities 14 and 16. After 15 seconds of vacuum pump operation, the system reads the sample pressure P provided by the absolute transducer 66 and starts the servo system "down" (removing gas from the chambers) with the initial set point pressure equal to the measured sample pressure. The pressure after 15 seconds would typically be down to about 50 mmHg. In block 4 of FIG. 7, a value labelled TIMEOUT is calculated as:

$$((P-20 \text{ Torr})/\text{Evac. Rate}) + 3 \text{ minutes}$$

where Evac. Rate is the rate of evacuation in Torr per second selected by the operator. Next, the servo set point pressure is decreased every second by the selected Evac. Rate so that the servo system begins to open the sample flow control valve 30 to allow gas to flow from the sample tube 20 into the first cavity 14. The servo system automatically opens the null-side flow control valve 35 so as to follow the effect of the operation of the sample flow control valve 30. The lowering of the set point pressure continues until the sample pressure is reduced to 20 Torr or until a time equal to TIMEOUT elapses. The software checks for this occurrence in block 6 and displays and error message on the LCD display 112 if the answer is that TIMEOUT has elapsed.

Assuming that the sample pressure is reduced to 20 Torr through the flow control valves, the sample and null-side vacuum valve pair 56/56 is opened to allow more rapid further evacuation of the sample and null tubes, and the Dewar 80 is lowered with the vacuum pump still operational and connected to the chambers. In block 9, the system monitors the sample pressure until it reaches 5 Torr, or provides an error message if the test of block 10 finds that 3 minutes have elapsed. If 5 Torr is reached, the system reads the sample pressure every 30 seconds until the difference in successive readings is less than 0.1 Torr. Then the vacuum pump continues to operate for an operator selected further evacuation time. In block 14, the valves 47 and 60/64 are closed, and the servo system is turned off with the flow control valves closed.

Under the now existing vacuum conditions, the current sample pressure is stored as a zero offset for the absolute pressure transducer 66, and the autozero circuit 137 is actuated to provide a correcting signal for the output of the chamber differential pressure transducer 40, to be used during sample runs. Finally, valves 56/57 are closed and the subroutine of FIG. 7 ends.

Returning to the "BALANCE SIDES" routine of FIG. 5, block 2 confirms that all valves are closed. Then valves 60/64 and 45 are opened to charge the cavities with helium for 5 seconds, after which the valve 45 is closed. After another 5 seconds to assure thermal equilibrium, the valves 60/64 are closed. Equal pressure of helium is now present in both cavities 14 and 16 and at both sides of the cavity differential transducer 17. After another 5 seconds, the output of the transducer 17 is read and stored as a zero offset for this transducer, which represents volume adsorbed during a sample run.

In block 7 of FIG. 5, a raise Dewar command is given to operate the Dewar motor for 15 seconds or until the upper limit switch is reached by the elevator 84. This immerses the sample and null tubes 20 and 25 in liquid nitrogen 81. Then the servo system is started in the "up" mode toward a set point pressure of 600 Torr to begin introducing helium into the tubes. In block 10, the sample pressure and pressure differential output of the transducer 17 (volume adsorbed signal) are read and displayed every second for the information of the operator, who is prompted by the LCD display to make a manual adjustment to the volume compensator 70. Since the flow control valves 30 and 35 maintain equal pressure on both sides below such valves, any difference in volume will result in a pressure differential between the cavities 14 and 16, giving rise to a volume adsorbed signal. If the volume adsorbed signal is reading positive, the operator should adjust the volume compensator piston 72 outwardly to increase the size of the null side until the volume adsorbed signal falls to or below 0. If the volume adsorbed signal is reading negative, the operator should adjust the volume compensator piston 72 inwardly to decrease the size of the null side.

Then the operator should depress the "Enter" key on the keypad 110, which will cause the set point pressure to be increased by 50 Torr (block 14) unless the set point pressure setting has reached 900 Torr (block 13). The operator is again prompted to adjust the volume under the new conditions. For most accurate balancing of the volumes, the operator should set up a positive volume adsorbed signal so that the final adjustment involves moving the piston 72 out of the cylinder 70. When balance is obtained to the operator's satisfaction, the "Escape" key is depressed to end the balancing routine by running a "Lower & Backfill" subroutine, described below in connection with FIG. 9.

Isolation of the cavities 14 and 16 from the chambers 20 and 25, respectively, by the valves 30 and 35, permits balancing of the volumes of the chambers with the sample present in the sample chamber. Such a procedure eliminates any effect of the sample free space as well as most of the effect of the non-ideal behavior of the adsorbate gas.

The routine for determining adsorption or desorption data for a sample is shown in FIG. 6, entitled "Analysis." First, the operator must attach a sample tube containing the sample 21 to be analyzed, and input several user-selected values, including (1) limits of the desired relative pressure range for the analysis, (2) the number of data points to record, (3) the mode of analysis—scanning or equilibrated steps, (4) an equilibration time constant in seconds between readings or analysis scan time in hours per analysis, (5) a pumpdown time at vacuum—Evac. Time, (6) the step down Evac. Rate in pressure/second or mmHg/minute for initial evacuation in blocks 4 and 5 of FIG. 7, (7) whether or not to utilize the software free space correction, (8) saturation pressure for the adsorbate, (9) identification and characteristics of the sample, and (10) requested data manipulation and report formats. As will be apparent, the target relative pressures for a stepped dose analysis can be calculated from (1) and (2) above. Also, the scan rate can be calculated by multiplying the highest relative pressure times the saturation pressure and dividing the product by the scan time.

In block 2 of FIG. 6, it is determined whether the operator wants the computer to generate and use a free space correction function using helium to measure any residual unbalance between the sides resulting from variations between sample tubes or the volume of the sample. A correction as a function of pressure is generated to be applied to the nitrogen volume adsorbed data. The first step toward generating this function is to run the "Evacuate, Lower & Zero" subroutine of FIG. 7. Then in blocks 4-8 of FIG. 6, the cavities 14 and 16 are filled with helium and a fresh zero offset for the volume adsorbed transducer 17 is determined in the manner described in connection with blocks 2-6 of FIG. 5.

Next, the "Dose & Equilibrate" subroutine of FIG. 8 is carried out to admit helium to the chambers 20 and 25 in similar manner to that by which nitrogen would be dosed during a run. All valves are closed, and the servo system is started in the "up" mode with the set point pressure set to the operator's initial target pressure. The circuit shown in FIG. 3 utilizes the output of the absolute pressure transducer 66 and of the differential transducer 40 to bring both chambers to the initial target pressure. If such pressure has not been reached within 3 minutes, a dosing error message is displayed. If the initial target pressure is reached, the system reads the volume adsorbed output of the differential pressure transducer 17 at intervals equal to the equilibration time constant specified by the operator. The CPU computes a 7-point Savitsky-Golay smoothed value of the volume adsorbed, and also the first derivative of the smoothed volume value. Then the system waits until the quotient of the derivative divided by the smoothed volume adsorbed is less than or equal to 0.0001. The smoothed volume adsorbed value meeting this criterion, and the current sample chamber pressure, are recorded for the first relative pressure.

In block 11 of FIG. 6, the above dosing and equilibrium process is repeated for the last of the operator's target pressures. The two data points for "volume adsorbed" using helium define a straight line correction function giving an amount to be subtracted from the volume adsorbed reading for each pressure at which data may be taken. The function is stored and the subtraction is done automatically by the system during actual runs.

After the free space correction function is determined, or if it is not requested, the "Evacuate, Lower & Zero" of FIG. 7 subroutine is executed. This removes the helium from the system and the system is now ready for an actual sample run. With all valves initially closed, the valves 60/64 and nitrogen valve 46 are opened to fill the cavities 14 and 16 with nitrogen from the tank 53. After 5 seconds, the valve 46 is closed, and after another 5 seconds, the valves 60/64 are closed. After an additional 5 seconds, the output of transducer 17 is measured and used as a zero offset for the volume adsorbed signal as described above.

In block 20 of FIG. 6, the Dewar is raised to lower the sample and null tubes to absorption temperature. Then the system calculates the interval between relative pressures at which data will be taken, and determines whether the analysis will be done in a scan mode or in a discrete point mode. If the latter has been selected, the data point locations in terms of absolute pressures to be measured by the transducer 66 are calculated. Then the "Dose & Equilibrate" subroutine of FIG. 8 is executed to obtain a pressure and volume adsorbed data point for the first target pressure. If the last target pressure has not been reached, the next target pressure is calculated and the "Dose & Equilibrate" subroutine is executed for the new target pressure. When all the requested data has been obtained, the "Lower & Backfill" subroutine of FIG. 9 is executed to terminate the analysis and bring the analyzer 10 to a safe holding status pending the next run.

Referring now to FIG. 9, in block 1 the servo system is stopped by changing the state of the signal on the line 134 from low to high. All valves are closed and the Dewar is lowered, which causes the adsorbed nitrogen on the sample 21 to begin to desorb. If the sample pressure does not reach 760 mmHg within 15 seconds, the servo system is turned on with a set pressure of 760 mmHg. When this set point pressure is reached or exceeded, or after 30 seconds, the servo system is stopped in block 6, and valves 60/64 and vacuum valve 47 are opened. The servo system is turned on again in the down mode with a set point pressure of 780 mmHg. When this target is reached, the servo system is turned off and the analyzer pressures are at safe levels for awaiting the next run. If, in block 3 of FIG. 9, the sample pressure is 760 mmHg or greater, the routine skips to block 6 and proceeds as described above.

If the scanning mode of dosing has been selected, the system waits for one minute to establish thermal equilibrium, and calculates the scan rate. In order to provide target pressures for data acquisition, the data point locations are calculated as for the discrete point mode. Then the servo system is operated "up" from zero pressure at the scan rate to the first servo set point. The pressure and volume adsorbed are recorded for the target pressures indicated by the operator, not necessarily at each servo set point. The lowest relative pressure for data acquisition may be zero, but need not be. One second after the pressure reaches the first servo set point, the servo set point is advanced by a pressure interval corresponding to the scan rate, and this is repeated until the scan has reached the last target pressure. If more than 3 minutes pass in attempting to come within 5 mmHg of any target pressure, an error message is displayed. The run is terminated as described above.

The computer can manipulate the digital data and present its calculations regarding surface area and pore volume in tabular or graphic form in a conventional manner. In addition to digital data acquisition as described, the analog output of the volume adsorbed differential transducer 17, via the conditioning circuit 115, can be connected to the chart recorder 155. The analog output of the absolute pressure transducer 66 can be converted to relative pressure and also connected to the chart recorder 155. This results in plotting the adsorption isotherm in real time.

It should be noted that the servo system will work equally well to remove gas from the sample and null chambers during desorption. Once saturation of the sample has occurred, the cavities 14 and 16 can be lowered in pressure so that opening the sample flow control valve 30 permits gas desorbed from the sample to flow into the sample cavity 14. The feedback circuit of FIG. 3 senses the inequality between the chambers, and opens the null-side flow control valve 35 to allow flow into the null-side cavity 16 until the pressure equalizes. Desorption can proceed under computer control similar to the manner described above in connection with adsorption, and a real time desorption isotherm can be plotted.

It will thus be seen that an analyzer embodying the present invention uses differential pressure transducers to obtain highly accurate adsorption or desorption data, and can eliminate the effect of sample volume, non-ideal gas behavior, and temperature changes of connecting passageways resulting from the evaporation of sample chamber coolant.

While this invention has been described in detail with particular reference to preferred embodiments thereof, it will be understood that variations and modifications can be effected within the spirit and scope of the invention as described hereinbefore and as defined in the appended claims.

What is claimed is:

1. A method for obtaining adsorption data, comprising the steps of:
    filling a first cavity and a second cavity with an adsorbing gas to the same pressure, the temperature in said first cavity being essentially equal to the temperature in said second cavity;
    admitting said gas from said first cavity into a sample chamber containing a sample capable of adsorbing said gas;
    admitting said gas from said second cavity into a null chamber until the pressure difference between said sample chamber and said null chamber is eliminated, the temperature in said sample chamber being essentially equal to the temperature in said null chamber; and
    measuring the pressure difference between said first and second cavities.

2. The method of claim 1, wherein said step of admitting said gas from said first cavity into said sample chamber comprises essentially continuously admitting said gas at a low rate.

3. The method of claim 2, wherein said step of admitting said gas from said second cavity into said null chamber comprises monitoring the pressure difference between said sample chamber and said null chamber and admitting gas from said second cavity into said null chamber as required to maintain said pressure difference between said sample chamber and said null chamber at zero.

4. The method of claim 1, further comprising the steps of:
continuing to admit said gas into said sample chamber from said first cavity until said sample is essentially saturated;
isolating and evacuating said first and second cavities;
admitting desorbed gas from said sample chamber into said first cavity;
admitting gas from said null chamber into said second cavity until the pressure difference between said sample chamber and said null chamber is eliminated; and
measuring the pressure difference between said first and second cavities.

5. The method of claim 4, wherein said step of admitting said gas from said sample chamber into said first cavity comprises continuously admitting said gas at a low rate.

6. The method of claim 5, wherein said step of admitting said gas from said null chamber into said second cavity comprises monitoring the pressure difference between said sample chamber and said null chamber and admitting gas from said null chamber into said second cavity as required to maintain said pressure difference between said sample chamber and said null chamber at essentially zero.

7. The method of claim 1, further comprising, prior to said step of filling said cavities with an adsorbing gas, the steps of:
filling said first and second cavities with a non-adsorbing gas to the same pressure;
admitting a quantity of said non-adsorbing gas from said first cavity to said sample chamber and then from said second cavity to said null chamber until the pressure difference between said sample chamber and said null chamber is eliminated; and
adjusting the volume of said null chamber until there is no pressure difference between said cavities.

8. An apparatus for obtaining adsorption data, comprising:
means for defining a first cavity and a second cavity having essentially equal volumes, the temperature in said first cavity being essentially equal to the temperature in said second cavity;
a sample chamber and a null chamber having essentially equal volumes, the temperature in said sample chamber being essentially equal to the temperature in said null chamber, said sample chamber being selectively connected to or isolated from said first cavity, and said null chamber being selectively connected to or isolated from said second cavity;
means for filling said first cavity and said second cavity with an adsorbing gas to the same pressure;
means for admitting said gas from said first cavity into said sample chamber containing a sample capable of adsorbing said gas;
means for admitting said gas from said second cavity into said null chamber until the pressure difference between said sample chamber and said null chamber, isolated, respectively, from said first and second cavities, is eliminated; and
means for measuring the pressure difference between said first and second cavities, isolated, respectively, from said sample and null chambers.

9. The apparatus of claim 8, wherein said means for admitting said gas from said first cavity into said sample chamber comprises means for continuously admitting said gas at a low rate.

10. The apparatus of claim 9, wherein said means for admitting said gas from said second cavity into said null chamber comprises means for monitoring the pressure difference between said sample chamber and said null chamber and for admitting gas from said second cavity into said null chamber as required to maintain said pressure difference between said sample chamber and said null chamber at essentially zero.

11. The apparatus of claim 8, further comprising:
means for filling said first and second cavities with a non-adsorbing gas to the same pressure, prior to the filling of said cavities with adsorbing gas;
means for admitting a quantity of said non-adsorbing gas from said first cavity to said sample chamber;
means for admitting a quantity of said non-adsorbing gas from said second cavity to said null chamber until the pressure difference between said sample chamber and said null chamber is eliminated; and
means for adjusting the volume of said null chamber until there is no pressure difference between said cavities.

12. The apparatus of claim 8, wherein said means for measuring the pressure difference between said first and second cavities comprises a first differential pressure transducer positioned between said cavities.

13. The apparatus of claim 12, wherein said means for admitting said gas from said second cavity into said null chamber until the pressure difference between said sample chamber and said null chamber is eliminated includes a second differential pressure transducer positioned between said sample chamber and said null chamber.

14. An apparatus for obtaining adsorption data, comprising:
means for defining a first cavity and a second cavity having essentially equal volumes, the temperature in said first cavity being essentially equal to the temperature in said second cavity;
a source of adsorbing gas;
fill valve means for admitting said adsorbing gas from said source into said cavities and for connecting or isolating said cavities to or from one another;
a sample chamber containing a sample capable of adsorbing said adsorbing gas;
a sample conduit connecting said first cavity to said sample chamber, said sample conduit including a sample dosing valve;
a null chamber;
a null-side conduit connecting said second cavity to said null chamber, said null-side conduit including a null-side dosing valve;
said sample and null chambers being selectively positionable in a liquid bath at a temperature at which adsorption of said gas occurs;
a first differential pressure transducer positioned to measure the difference in pressure between said first and second cavities;
a second differential pressure transducer positioned to measure the difference in pressure between said sample chamber and said null chamber;
an absolute pressure transducer positioned to measure the pressure in said sample chamber; and
means for evacuating said apparatus.

15. The apparatus of claim 14, further comprising:
control means for:

operating said evacuating means to evacuate said apparatus;

operating said fill valve means to fill said first and second cavities with said adsorbing gas to the same pressure and then to isolate said cavities from one another;

operating said sample dosing valve to admit said gas into said sample chamber;

operating said null-side dosing valve to admit said gas into said null chamber until the output of said second differential pressure transducer is essentially zero; and reading the output of said first differential pressure transducer.

16. The apparatus of claim 15, wherein said control means operates said sample dosing valve so as to admit said gas from said first cavity into said sample chamber essentially continuously at a low rate.

17. The apparatusof claim 16, wherein said control means operates said null-side dosing valve so as to admit said gas from said second cavity into said null chamber as required to maintain the output of said second differential pressure transducer at essentially zero.

18. The apparatus of claim 15, wherein said control means operates said sample dosing valve so as to admit said gas from said first cavity into said sample chamber until the pressure within said sample chamber reaches a target pressure.

19. The apparatus of claim 18, wherein said control means operates said null-side dosing valve so as to admit said gas from said second cavity into said null chamber as required to maintain the output of said second differential pressure transducer at essentially zero.

20. The apparatus of claim 15, further comprising:
a source of non-adsorbing gas; and
means for altering the volume of said null chamber; and
wherein said control means is operative, prior to filling said cavities with said adsorbing gas, to fill said cavities with said non-adsorbing gas to the same pressure, to isolate said cavities from one another, to permit said non-adsorbing gas to expand into said sample chamber from said first cavity and into said null chamber from said second cavity to essentially equalized the pressure in said chambers, such that said means for altering the volume of said null chamber may be operated until the output of said first differential pressure transducer is essentially zero.

21. The apparatus of claim 14, further comprising means for altering the volume of said null chamber.

22. The apparatus of claim 21, further comprising means for altering the volume of said sample chamber.

23. A method for obtaining adsorption data, comprising the steps of:

filling a first cavity and a second cavity with an adsorbing gas to the same pressure, the temperature in said first cavity being essentially equal to the temperature in said second cavity;

admitting said gas from said first cavity into a first chamber;

admitting said gas from said second cavity into a second chamber;

one of said first and second chambers containing a sample capable of adsorbing said gas, and the temperature in said first chamber being essentially equal to the temperature in said chamber;

adjusting the amount of said gas admitted into said chambers until the pressure difference between said chambers is essentially eliminated; and measuring the pressure difference between said first and second cavities.

24. The method of claim 23, further comprising, prior to admitting adsorbing gas into said cavities, the steps of:

admitting a non-adsorbing gas into said chambers; and adjusting the volume of either one of said chambers.

25. The method of claim 23, wherein said first and second cavities have essentially equal volumes, and wherein said first and second chambers have essentially equal volumes.

26. An apparatus for obtaining adsorption data, comprising:

means for defining a first cavity and a second cavity;

means for filling said first cavity and said second cavity with an adsorbing gas to the same pressure, the temperature in said first cavity being essentially equal to the temperature in said second cavity;

means for admitting said gas from said first cavity into a first chamber and for admitting said gas from said second cavity into a second chamber;

one of said first and second chambers containing a sample capable of adsorbing said gas, the temperature in said first chamber being essentially equal to the temperature in said second chamber;

means for adjusting the amount of said gas admitted into said chambers until the pressure difference between said chambers is essentially eliminated; and means for measuring the pressure difference between said first and second cavities.

27. The apparatus of claim 26, further comprising:
means for adjusting the volume of either one of said chambers.

28. The method of claim 26, wherein said first and second cavities have essentially equal volumes, and wherein said first and second chambers have essentially equal volumes.

* * * * *